(12) United States Patent
Nagai et al.

(10) Patent No.: US 8,830,483 B2
(45) Date of Patent: Sep. 9, 2014

(54) OPTICAL COHERENCE TOMOGRAPHY WITH REFRACTIVE INDEXING OF OBJECT

(75) Inventors: Fumio Nagai, Kunitachi (JP); Soh Ohzawa, Toyonaka (JP)

(73) Assignee: Konica Minolta Opto, Inc., Tokyo (JP)

( * ) Notice: Subject to any disclaimer, the term of this patent is extended or adjusted under 35 U.S.C. 154(b) by 637 days.

(21) Appl. No.: 13/125,910

(22) PCT Filed: Sep. 4, 2009

(86) PCT No.: PCT/JP2009/065488
§ 371 (c)(1),
(2), (4) Date: Apr. 25, 2011

(87) PCT Pub. No.: WO2010/050296
PCT Pub. Date: May 6, 2010

(65) Prior Publication Data
US 2011/0222070 A1    Sep. 15, 2011

(30) Foreign Application Priority Data

Oct. 29, 2008   (JP) ................................ 2008-278511

(51) Int. Cl.
*G01B 9/02* (2006.01)
*G01N 21/47* (2006.01)
*A61B 5/00* (2006.01)

(52) U.S. Cl.
CPC .............. *G01B 9/02* (2013.01); *G01N 21/4795* (2013.01); *A61B 5/0066* (2013.01)
USPC ......................................... 356/517; 356/497

(58) Field of Classification Search
CPC .......................... G01B 9/02064; A61B 3/102
USPC .................. 356/479, 497, 504, 517
See application file for complete search history.

(56) References Cited

U.S. PATENT DOCUMENTS 5,469,291 A * 11/1995 Plesko ...................... 359/224.1
7,511,822 B2    3/2009 Fujita

FOREIGN PATENT DOCUMENTS

| CN | 101049232 | 10/2007 |
|---|---|---|
| JP | 11-108763 | 4/1999 |
| JP | 2003-035660 | 2/2003 |
| JP | 2005-300488 | 10/2005 |
| JP | 2007-085931 | 4/2007 |
| JP | 2007-151631 | 6/2007 |
| JP | 2008194106 A * | 8/2008 |

OTHER PUBLICATIONS

M. Ohmi et al., "Simultaneous Measurement of Refractive Index and Thickness of Transparent Plates by Low Coherent Interferometry", Optical Review, Jul. 1997, vol. 4, No. 4, pp. 507-515.

* cited by examiner

*Primary Examiner* — Hwa Lee
(74) *Attorney, Agent, or Firm* — Cozen O'Connor

(57) ABSTRACT

An optical tomographic image forming method including: splitting low coherence light emitted from a light source is split into a measuring light and a reference light; forming an optical tomographic image of a measured object by detecting an interference light that is obtained by superposing reflected light, reflected from the measured object when the measuring light is irradiated onto the measured object via a condenser lens, and reflected light, reflected from a reference mirror, which is positioned a predetermined length of optical path away from the splitting position, when the reference light is irradiated onto the reference mirror, wherein the method further includes: inputting a refractive index of the measured object; correcting the tomographic image in accordance with the inputted refractive index of the measured object; and outputting the corrected tomographic image.

6 Claims, 6 Drawing Sheets

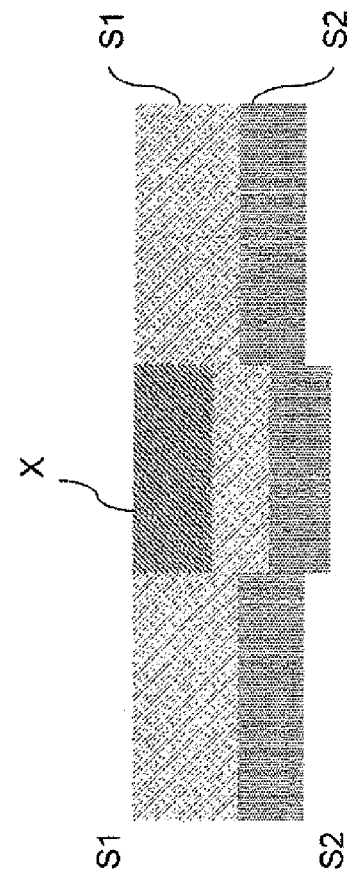
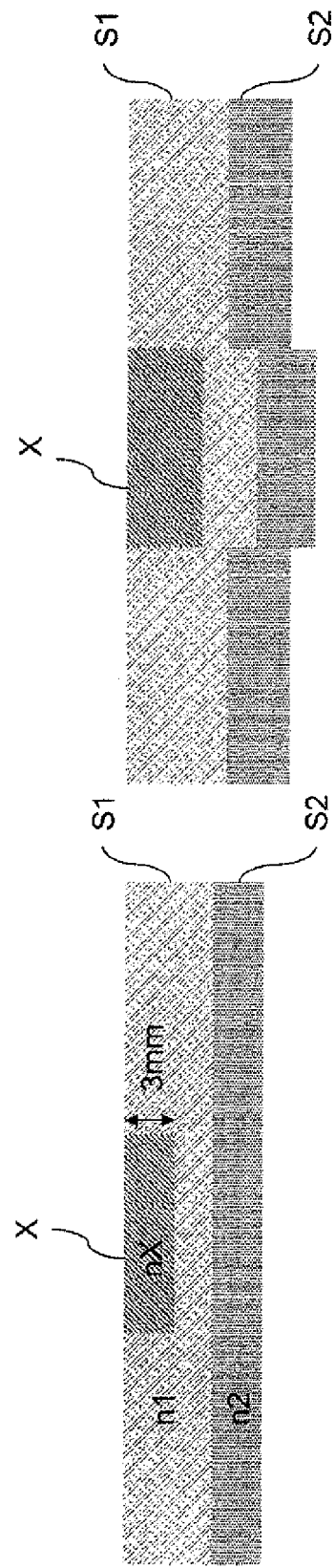
FIG. 5a
FIG. 5b

OPTICAL COHERENCE TOMOGRAPHY WITH REFRACTIVE INDEXING OF OBJECT

RELATED APPLICATIONS

This application is a U.S. National Phase Application under 35 USC 371 of International Application PCT/JP20091065488 filed Sep. 4, 2009.

This application claims the priority of Japanese application No. 2008-278511 filed Oct. 29, 2008, the entire content of which is hereby incorporated by reference.

TECHNICAL FIELD

This invention relates to an optical tomography image forming method for generating optical tomographic images by using OCT (Optical Coherence Tomography) measurement.

BACKGROUND TECHNOLOGY

Recently, as an endoscope apparatus for observing the inside of a body cavity of a living body, electronic endoscope apparatuses which obtain an image of a living body based on reflected light reflected from a living body which is irradiated by an illuminating light, and display the image on a monitor, or the like, have come into wide use in various field. Also, many endoscope apparatuses include a forceps port, and via a probe introduced into the body cavity through this forceps port, the biopsy and treatment of tissues in the body cavity can be performed.

As the above-described endoscope apparatus, an ultrasonic tomographic imaging apparatus that uses an ultrasonic wave and the like are also known. Further, as an example, an optical tomographic imaging apparatus that employs light interference of low coherence light may also be used. In those optical tomographic imaging apparatuses, a low coherence light emitted from a light source is split into a measuring light and a reference light. Thereafter, reflected light, which is the measuring light reflected by a measured object when the measuring light is irradiated onto the measured object, is guided to a light multiplexing means. Meanwhile, the reference light is guided to the light combining after the optical path length thereof is changed. Then, the reflected light is combined with the reference light via the light combining means, and the interference light produced by the mixing of the reflected light with the reference light is measured via heterodyne detection or the like.

Further, when the measuring light is irradiated onto the measured object, a probe is used, the probe which is inserted into the body cavity from a forceps through a forceps channel. The probe includes an optical fiber for guiding the measuring light and a rotatable mirror which is provided at the tip of the optical fiber for reflecting the measuring light in the orthogonal direction. The measuring light is irradiated on the measured object in the body cavity from the probe, and the reflected light reflected from the measured object is guided to the light combining means again through the optical fiber of the probe. Here, by utilizing the fact that interference light is detected when the optical path lengths of the measuring light and the reflected light equate to the optical path length of the reference light, the measuring position (the depth of measurement) in the measured object is changed, by changing the optical path length of the reference light. This is a so-called OCT measurement (refer to Patent Document 1).

PRIOR ART DOCUMENT

Patent Document

Patent Document 1: Unexamined Japanese Patent Application No. 2007-85931

SUMMARY OF THE INVENTION

Problems to be Solved by the Invention

In this OCT measurement, information on the depth direction of a measured object is obtained from the difference in the optical path length of the optical path length of the measuring light and the optical path length of the reference light. However, because human tissue, which is a measured object of OCT measurement, or the like, is generally different from air in refractive index, there is a possible problem in that, when the measuring light passes through the interior of the measured object, the optical path length varies in accordance with the refractive index. Thereby, when a tomographic image is formed by using the measured OCT values themselves, the actual distance does not match the optical path length due to differences in refractive index, resulting in a distortion on the formed tomographic image compared to the actual tissue.

The present invention has been achieved in consideration of the above-described problem, and an object of the present invention is to provide an optical tomographic image forming method capable of obtaining a tomographic image closer actuality.

Means to Solve the Problems

The optical tomographic image forming method of item 1, is one in which a low coherence light emitted from a light source is split into a measuring light and a reference light, and an optical tomographic image of a measured object is formed by detecting the interference light that is obtained by superposing reflected light; reflected from the measured object when the measuring light is irradiated onto the measured object via a condenser lens; and reflected light, reflected from a reference mirror, being positioned a predetermined optical path length away from the splitting position, when the reference light is irradiated onto the reference mirror, wherein, a refractive index of the measured object is inputted, and the optical tomographic image is corrected in accordance with the inputted refractive index of the measured object, and outputted.

According to the present invention, more real optical tomographic image with less distortion can be acquired in such a manner that a refractive index of the measured object is inputted, and the optical tomographic image is corrected in accordance with the inputted refractive index, and then outputted.

The optical tomographic image forming method of item 2 is as set forth in item 1, and wherein a known datum is inputted as the refractive index of the measured object. The term "known datum" is datum of the refractive index of tissue closer to that of the measured object, and other refractive indexes which have been obtained via experiments, or the like.

The optical tomographic image forming method of item 3 is as set forth in item 1 or 2, and wherein, in a case in which the measuring light is obliquely incident upon a first reflecting surface of the measured object, an optical path length, through which the measuring light passes, of a case in which the measuring light is refracted at the first reflecting surface and then reflected at a second reflecting surface of the measured object, is set as the optical path length between the first reflecting surface and the second reflecting surface, assuming that the measuring light travels in a straight line inside the measured object regardless of the incident angle of the measuring light, and the optical tomographic image is corrected in accordance with the refractive index between the first reflecting surface and the second reflecting surface, and then outputted. Note that, in this Specification, "the second reflecting surface" is positioned inside the measured object so as to be inwardly positioned behind "the first reflecting surface", and includes the surface of the measured object.

The optical tomographic image forming method of item 4 is as set forth in item 1 or 2, and wherein, in a case in which the measuring light is obliquely incident upon a first reflecting surface of the measured object, an optical path length, through which the measuring light passes, of a case in which the measuring light is refracted at the first reflecting surface and then reflected at a second reflecting surface of the measured object, is determined in accordance with: the incident angle of the measuring light upon the first reflecting surface; the refractive index of incident side of the first reflecting surface; and the refractive index between the first reflecting surface and the second reflecting surface, and the optical tomographic image is corrected and then outputted.

The optical tomographic image forming method of item 5 is as set forth in any one of items 1 through 3, and wherein a refractive index of the measured object is obtained from the difference between a first position and a second position, the first position in which the measured object, or said condenser lens and said reference mirror are moved so as to maximize the intensity of an interference light of reflected light, reflected from the first reflecting surface, and reflected light from the reference mirror, and the second position in which the measured object or the condenser lens and the reference mirror are moved so as to maximize the intensity of an interference light of a reflected light, reflected from the second reflecting surface, and a reflected light from the reference mirror.

The optical tomographic image forming method of item 6 is as set forth in any one of items 1 through 5, and wherein coherency distance $\Delta l$ of the low coherence light, which is expressed by the following equation, is less than or equal to 30 μm:

$$\Delta l = 2(\ln 2)\lambda_o^2/(\pi \Delta\lambda)$$

where $\lambda_o$: Center wavelength of said low coherence light, and
$\Delta\lambda$: Bandwidth of said low coherence light (range of intensity more than half of the maximum intensity).

Effects of the Invention

According to the present invention, it becomes possible to provide an optical tomographic image forming method capable of obtaining a tomographic image closer to actuality.

BRIEF DESCRIPTION OF THE DRAWINGS

FIG. 5a is a schematic diagram of a cross-sectional image of actual tissue of a measured object, and FIG. 5b is a schematic diagram of an optical tomographic image of measured object S, obtained via a tomographic signal.

DESCRIPTION OF THE PREFERRED EMBODIMENT

Figure 1:
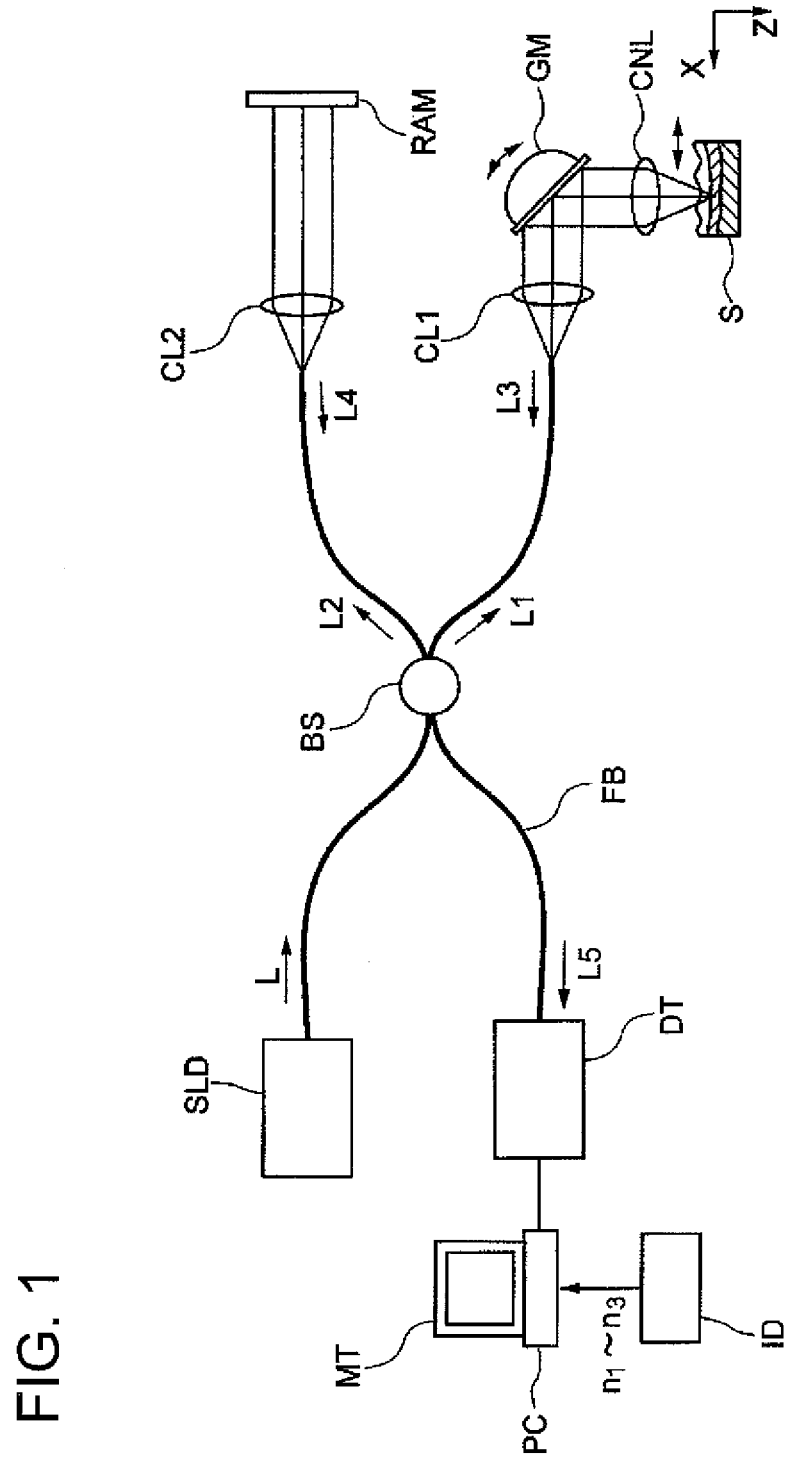
FIG. 1 is a schematic diagram of an optical tomographic image measuring apparatus capable of using an optical tomographic image forming method according to the present embodiment.

Hereinafter, the preferred embodiment of the present invention will be described in detail with reference to the drawings. FIG. 1 is a schematic diagram of an optical tomographic image measuring apparatus capable of using an optical tomographic image forming method according to the present embodiment. The optical tomographic image measuring apparatus consists of light source SLD for emitting low coherent light L, beam splitting means BS for splitting low coherent light L into measuring light L1 and reference light L2, first collimator CL1 for converting measuring light L1, having been split by optical beam splitting means BS, to parallel luminous fluxes, galvano mirror GM for reflecting measuring light L1, having been emitted from first collimator CL1, condenser lens CNL for condensing measuring light L1, having been reflected at galvano mirror GM, onto measured object S, second collimator CL2 for converting reference light L2, having been split by optical beam splitting BS, to parallel luminous fluxes, reference mirror RAM for totally reflecting reference light L2, having been emitted from second collimator CL2, interference light detecting means DT for detecting superposed interference light, having been superposed when reflected light of measuring light L1 from measured object S and reflected light of reference mirror RAM are returned again to beam splitting means ES, and personal computer PC for forming an optical tomographic image onto monitor MT in accordance with data from inputting means ID, and information from interference light detecting means DT. Note that light source SLD, first collimator CL1, second collimator CL2, and interference light detecting means DT are connected via optical fiber FB, and light propagates inside optical fiber FB.

Here, light source SLD is composed of, for example, a laser light source which emits low coherent light such as SLD (Super Luminescent Diode), ASE (Amplified Spontaneous Emission), or the like. Note that because the optical tomographic image measuring apparatus is to obtain a tomographic image of measured object S which is a living body, such as the inside of a body cavity, or the like, a light source, which is capable of minimizing attenuation of light due to scattering and absorption when light propagates through the interior of measured object S, is used. As an example, an ultra-short pulse laser light source with a wide spectral range, and of which the center wavelength is 1.3 μm while propagating through a living body, or the like, is preferably used. Also, the coherency distance $\Delta l$ of low coherence light is preferably not more than 30 μm because the spatial resolution of measurement is preferred to be no more than 30 μm in case of the measurement of a living body.

$$\Delta l = 2(\ln 2)\lambda_o^2/(\pi \Delta\lambda)$$

where $\lambda_o$: Center wavelength of said low coherence light, and $\Delta\lambda$: Bandwidth of low coherence light (range of intensity more than half of the maximum intensity). Beam splitting means BS is composed of, for example, an optical fiber coupler of 2×2, and it is so configured that low coherent light L, guided from light source SLD via optical fiber FB, is split into measuring light L1 and reference light L2.

Reference light L2 is reflected at reference mirror RAM, and is incident upon beam splitting means BS again as reflecting light L4. Also, reflecting light L3, which is measuring light L1 reflected from the boundary between the refractive indices of internal tissue of measured object S, is incident upon beam splitting means BS again. When a total of optical path lengths of measuring L1 and reflecting light L3, and a total of optical path lengths of reference L2 and reflecting light L4, are approximately the same, reflecting light L3, having been incident upon beam splitting means BS, and reflecting light L4 are superposed and interfered. Superposed light L5, having been superposed, is incident upon detector DT and converted into electric signals, and detected.

An operation of optical tomographic image measuring apparatus 1 will be described. In FIG. 1, low coherent light L, emitted from light source SLD, propagates the interior of optical fiber FB, and is split into measuring light L1 and measuring light L1 and reference light L2 at beam splitting means BS. Measuring light L1, having been split via beam splitting means BS, propagates the interior of optical fiber FB, and is emitted from the edge face of the fiber toward first collimator CL1, and is reflected via galvano mirror GM, and condensed from condenser lens toward measured object S. Measuring light L3, having been reflected by internal tissue of measured object S, passes through condenser lens CNL again, is reflected at galvano mirror GM, and enters from the edge face of optical fiber FB into the inside of the fiber, and reaches interference light detecting means DT. Meanwhile, reference light L2, having been split via beam splitting means BS, propagates the interior of optical fiber FB, and is emitted from the edge of the fiber toward second collimator CL2, and is reflected via reference mirror RAM, is guided from the edge of optical fiber FB into the interior of the fiber again via second collimator CL2, and reaches interference light detecting means DT. Reflecting light L3 of the measuring light and reflecting light L4 of the reference light, having been superposed via beam splitting means BS, are detected via interference light detecting means DT, and a tomographic signal is accordingly generated. Note that tomographic information within a predetermined range of measured object S can be obtained by scanning while rotating galvano mirror GM.

Figure 2:
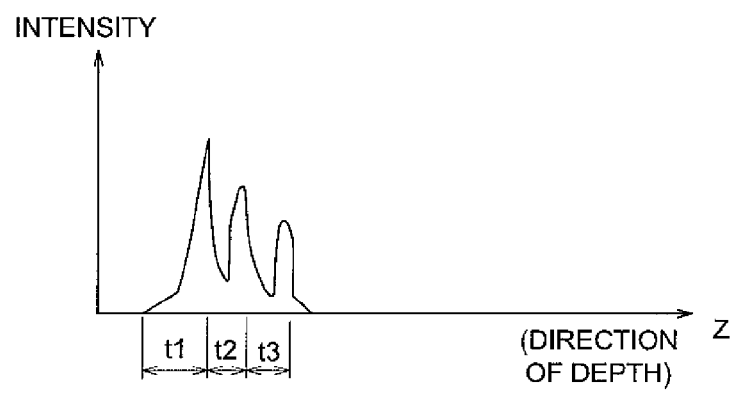
FIG. 2 is a figure showing a tomographic signal obtained via interference light detecting means DT shown in FIG. 1.

FIG. 2 is a figure showing a tomographic signal, obtained via interference light detecting means DT shown in FIG. 1, after signal processing was carried out. Here, measuring light L1 generates reflecting light at different positions in accordance with the boundary surface of refractive indices of internal tissue of measured object S.

Figure 3A:
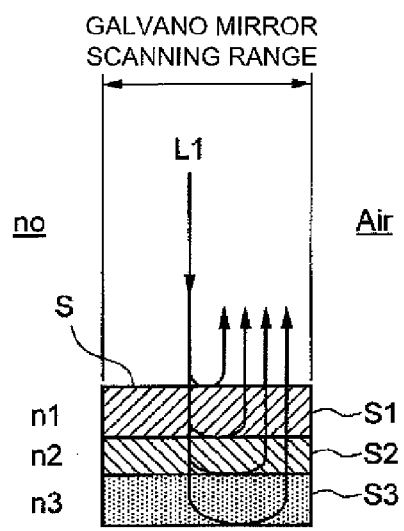
FIG. 3a is a schematic diagram of a cross-sectional image of actual tissue of measured object S.
Figure 3B:
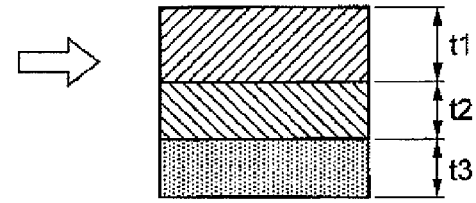
FIG. 3b is a schematic diagram of an optical tomographic image of measured object S, obtained via the tomographic signal.

Here, a diagram of a cross-sectional image of actual tissue of measured object S is schematically shown in FIG. 3a, and a diagram of an optical tomographic image of measured object S, obtained via OCT apparatus, or the like, is schematically shown in FIG. 3b. As shown in FIG. 3a, in a case in which measured object S is composed of 3 layers of tissue S1 to S3, when the measuring light is irradiated onto measured object S, reflecting light is generated at four places, the boundary surface of air and first layer S1, the boundary surface of first layer S1 and second layer S2, the boundary surface of second layer S2 and third layer S3, and boundary surface of third layer S3 and the rear surface.

Thereby, when an optical tomographic image of the measured object is formed by obtaining the thickness of each layer t1 through t3 directly from an interval between peak values of the tomographic signal shown in FIG. 2, and rotating galvano mirror GM, the optical tomographic image becomes the one as shown in FIG. 3b. However, since the thickness of each layer t1 through t3 in the optical tomographic image is different from the actual values, such optical tomographic image is different from actual tissue, and has elongated distortion in the depth direction. Here, if the refractive index of air is set to "n0", the refractive index of first layer S1 is set to "n1" ($\neq$n0, n2), the refractive index of second layer S2 is set to "n2" ($\neq$n0, n1, n3), and the refractive index of third layer S3 is set to "n3" ($\neq$n0, n2), then the optical path length of measuring light L1 to pass through first layer S1 is (n1/n0) times the optical path length of measuring light L1 to pass through air. Also the optical path length of measuring light L1 in case it travels through second layer S2 is (n2/n0) times the optical path length of measuring light L1 to pass through air, and the optical path length of measuring light L1 to pass through third layer S3 is (n3/n0) times the optical path length of measuring light L1 to pass through air. Then, in this embodiment, the obtained optical tomographic image is corrected to become closer to actual tissue (namely, a length correction are carried out for the optical path length of light, passing through the measured object, to obtain an actual distance, and then the optical tomographic image is converted based on the obtained actual distance, and outputted). More specifically, refractive indices n1 to n3 of the first to third layers S1 through S3 are inputted via input means ID, and, in personal computer PC, a correction with respect to the optical tomographic images, obtained from the tomographic signals, is carried out in such a manner that the optical path length of measuring light L1, in case of passing through first layer S1, is multiplied by (n0/n1), also, the optical path length of measuring light L1, in case of passing through second layer S2, is multiplied by (n0/n2), and the optical path length of measuring light L1, in case of passing through third layer S3, is multiplied by (n0/n3). The refractive indexes n1 to n3 of the first to third layers S1 through S3 can be exemplified by either the refractive index which is actually measured in tissue extracted via surgical operation, or the refractive index of a substance similar in components, or the like.

Particularly, as shown in FIG. 5a, in a case in which small foreign material X of refractive index nX exists in a material which is composed of first layer S1 of refractive index n1 and second layer S2 of refractive index n2, and the boundary surface between the layers exists at a position 3 mm deep from the surface of the tissue, distortion of 3×(nX−n1) mm may arise on the tomographic image. Here, if the resolution capability of OCT measurement is "10 μm=0.01 mm", in a case in which the difference of refractive index (nX−n1) between foreign material X and the first layer is more than or equal to "3/0.01=0.003", then there is a possibility that the distortion may have an adverse influence on the tomographic image. When explained by the concrete example, in the case of actual tissue as shown in FIG. 5a, even if the boundary surface between first layer S1 and second layer S2 continues smoothly, due to the influence of the distortion, like the tomographic image shown in FIG. 5b, there is a possibility in that it is displayed as if the boundary surface between first layer S1 and second layer S2 is shifted at the back side of foreign material X. For this eventuality, according to the present invention, it is capable of displaying a tomographic image of tissue, which is closer to the actual tissue, by carrying out the above-described correction.

Further, in another modified example, in a case in which at least two reflection surfaces (a first reflecting surface and a second reflecting surface) in the direction of depth of measured object S, the refractive index of measured object S may be obtained from the difference between a first position; in which said measured object, or said condenser lens and said reference mirror are moved so as to maximize the intensity of interference light of reflected light L3, reflected from the first reflecting surface of measured object S, and reference light L; and a second position, in which said measured object or said condenser lens and said reference mirror are moved so as to maximize the intensity of interference light of said measuring light, reflected from the second reflecting surface of said measured object, and said reference light. In this case, image correction by refractive indexes can be simultaneously carried out by also measuring tomographic images while measuring the refractive index via the OCT apparatus.

Figure 7:
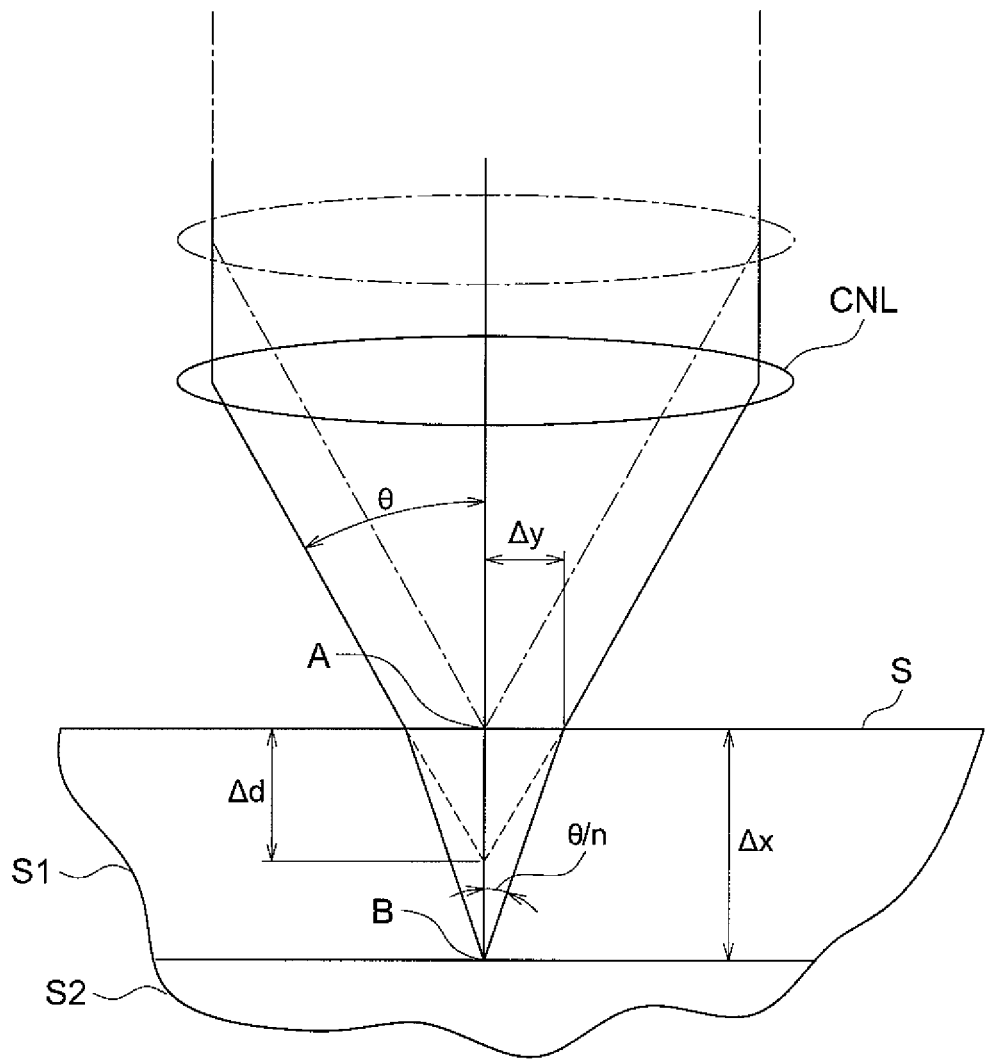
FIG. 7 is a schematic diagram explaining a summary of a method for obtaining the refractive index of measured object S.

A method for obtaining the refractive index of measured object S will be described more concretely. FIG. 7 is a schematic diagram explaining a summary of the method for obtaining the refractive index of measured object S. The method for obtaining the refractive index of measured object S consists of two steps, a first step and a second step.

Firstly, the first step is explained. As shown by the alternate long and short dashed line in the figure, the position of condenser lens CNL or the position of measured object S is controlled by using an actuator, which is not shown in the figure, so that the outgoing light emitted light from condenser leans CNL is condensed onto spot A on the boundary surface between the first layer and air. When the outgoing light emitted from condenser lens CNL is condensed upon spot A, the light intensity of reflected light L3, returning to optical fiber FB, is maximized, and therefore, personal computer PC controls the position of condenser lens CNL or the position of measured object S by monitoring the light intensity of reflected light L3, returning to optical fiber FB.

Secondly, as shown by the solid line in the figure, the position of condenser lens CNL or the position of measured object S is controlled by using the actuator, which is not shown in the figure, so that the outgoing light emitted light from condenser leans CNL is condensed onto spot B on the boundary surface between the first layer and the second layer. When the outgoing light emitted from condenser lens CNL is condensed upon spot B, the light intensity of reflected light L3, returning to optical fiber FB, is maximized, and therefore, personal computer PC controls the position of condenser lens CNL or the position of measured object S by monitoring the light intensity of reflected light L3, returning to optical fiber FB. In such a way, personal computer PC obtains $\Delta d$ after condensing the outgoing light, emitted from condenser lens CNL, onto spots A and B.

Here, converging angle of the light emitted from condenser lens CNL is set to $\theta$, the refractive index of first layer S1 is set to "n", and the thickness of first layer S1 is set to $\Delta x$. The distance between the boundary of first layer S1 and air, and the converging spot of the light emitted from condenser lens CNL, in a case in which the refractive index of first layer S1 is 1, is set to $\Delta d$. The radius of light diameter of the light, emitted from condenser lens CNL, at the boundary between first layer S1 and air, is set to $\Delta y$. By assuming that $\theta$ has a sufficiently small value, the conversing angle inside first layer S1 is indicated as $\theta/n$ as shown in the figure. From the foresaid assumption, the formulas $[\Delta x = \Delta y/\tan(\theta/n) \approx \Delta y/(\theta/n)]$ and $[\Delta y = \Delta d \times \tan\theta \approx \Delta d \times \theta]$ can be obtained. From these two formulas, the formula of "$\Delta x = n \times \Delta d$" can be obtained. Note that $\Delta d$ is a known amount which personal computer PC can obtain as mentioned above.

Next, the second step will be described. The outgoing light, emitted from condenser lens CNL, is condensed onto spot A, for example. Then, under this condition, reference mirror RAM is moved so as to maximize the light intensity of superposed light L5. The position of reference mirror RAM is memorized by personal computer PC. Because the outgoing light emitted from light source SLD is a low coherent light, the light intensity of superposed light L5 is maximized only when the optical path lengths of reflecting lights L3 and L4 become equal.

Next, the outgoing light, emitted from condenser lens CNL, is condensed onto spot B. Under this condition, reference mirror RAM is moved so as to maximize the light intensity of superposed light L5, and that position is memorized by personal computer PC. Then, personal computer PC obtains distance $\Delta d'$, between those two positions, having been memorized. This $\Delta d'$ satisfies the following formula: $\Delta d' = n \times \Delta x$. From the formula: $\Delta d' = n \times \Delta x$ and the previously-obtained formula: $\Delta x = n \times \Delta d$, the formula: $n = (\Delta d'/\Delta d)^{1/2}$ is obtained.

Thereby, by obtaining $\Delta d'$ and $\Delta d$, the refractive index "n" can be calculated.

Figure 4:
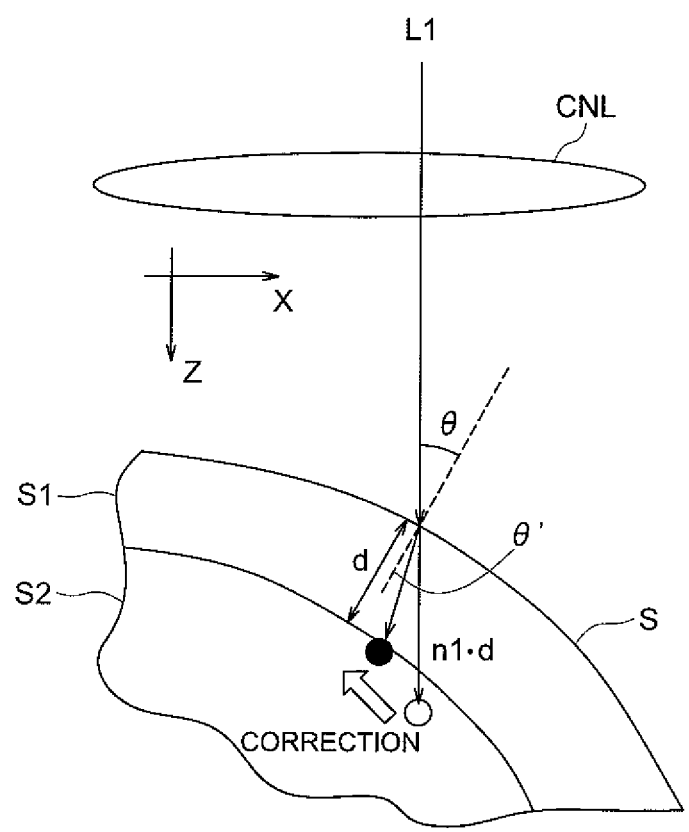
FIG. 4 is a schematic diagram showing a first correction method in a case in which the surface of measured object S is a curved-surface.

Next, a correction of tomographic image will be described in a case in which the surface of measured object S is a curved-surface, or the like, and the measuring light is obliquely incident upon the surface. FIG. 4 is a schematic diagram showing a first correction method in a case in which the surface of measured object S is a curved-surface. In a case in which the surface of first layer S1 of measured object S is a curved-surface, if the light beam, emitted from condenser lens CNL, is obliquely incident upon measured object S with angle $\theta$ with respect to the normal line of the surface of first layer S1 (the first reflecting surface) of measured object S, the light beam is refracted by an angle $\theta'$ based on the difference between refractive index n1 of first layer S1 and the refractive index n0 of air. In this case, the optical path length varies when compared with a case in which measuring light L1 travels in a straight line and reflected at the surface (the second reflecting surface) of second layer S2. Then, the optical path length, having been varied, is to be corrected.

More specifically, because formula: $[n0 \times \sin\theta = n1 \times \sin\theta']$ is satisfied, in FIG. 4, in a case in which the direction of the optical axis is set to "z" direction, and the direction perpendicular to the optical axis is set to "x" direction, and the distance (not the optical path length, but the actual distance) from the surface of first layer S1 to the surface of second layer S2 through which the outgoing light beam emitted from condenser lens CNL passes, is assumed to be "d", the reflection point on the surface of second layer S2 shifts by ["d"$\times\sin(\theta-\theta')$] in the direction of"-x", and [n1$\times$"d"$\times\cos(\theta-\theta')$] in the direction of "-y", and therefore, it is preferable to correct the optical path length correspondingly, via personal computer PC. In this example, although tomographic images can be formed more precisely, a longer time is required for processing because the incident angle of measuring light L1 needs to be obtained, in addition to the difference between refractive indexes. Meanwhile, according to the following image processing, a correction, by using only the difference in refractive indexes, can be made in a shorter time.

Figure 6:
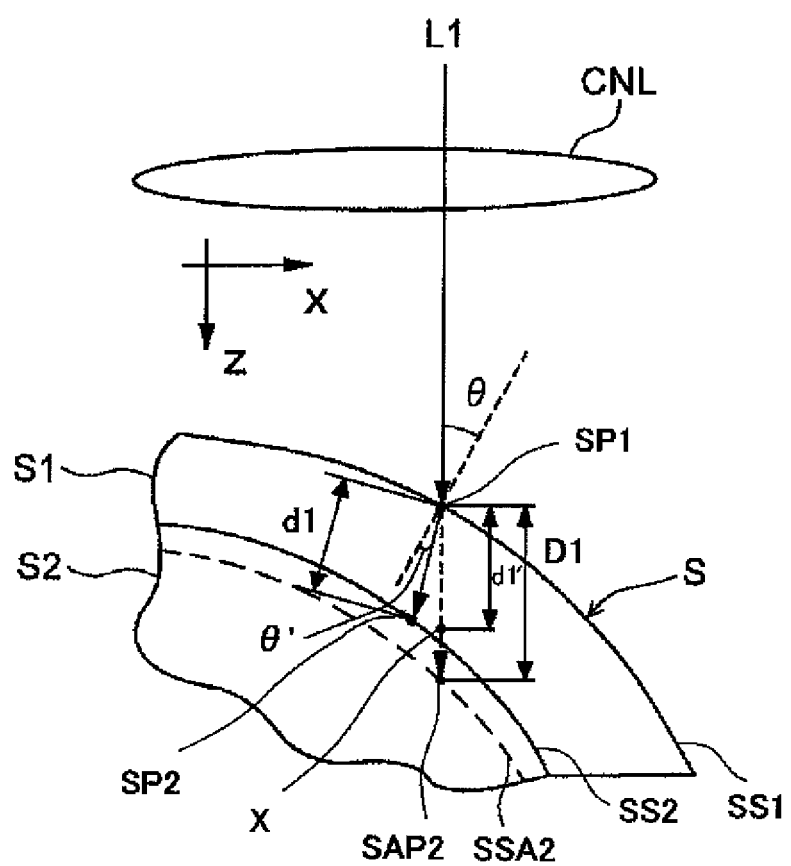
FIG. 6 is a schematic diagram showing a second correction method in a case in which the surface of measured object S is a curved-surface.

FIG. 6 is a schematic diagram showing a case in which measuring light L1 is obliquely incident upon surface SS1 (first reflecting surface) of first layer S1 of measured object S, with an incident angle of $\theta$, and passes through first layer S1, and then reflected or scattered at boundary surface SS2 (second reflecting surface) between first layer S1 and second layer S2. Spot SP1 is an intersection point of measuring light L1 and surface SS1, spot SP2 is an intersection point of measuring light L1 and boundary surface SS2. The optical path length from spot SP1 to spot SP2 through which measuring light L1 passes, is set to "D1". Namely, D1=d1×n1 (where, d1 is the distance in which measuring light L1 passes through first layer S1). Here, the spot, where the light, which was incident upon surface SS1, traveled optical path length D1 in a straight line without being refracted, is set to spot SAP2. Also, in a case in which surface SS1 of measured object S is scanned by measuring light L1, the cluster of spot SAP2 is indicated by image surface SSA2. As an example, when measurement is performed by an OCT apparatus, regardless of refraction at a surface or the refractive index of a medium, the light, which is reflected, or scattered light of the measuring light from the reflecting surface inside the medium, is observed by being considered that the measuring light travels in a straight line inside the medium, and also the refractive index of the medium is equal to the spatial refractive index. In other words, boundary surface SS2 is measured as image surface SSA2, resulting in distortion errors between the actual measured object and the observed tomographic image.

According to the embodiment, the positions of spot SP1 and spot SAP2 are corrected in accordance with refractive index n0 of air, which is on the incidence side of surface SS1, and refractive index n1 of first layer S1. More specifically, image correction is carried out via personal computer PC assuming that the measuring light is reflected at spot SP2, not at position (X) where the measuring light travels distance d1' from spot SP1 in a direction of straight line. Here, distance d1' becomes a length closer to the configuration of actual measured object, and calculated as: d1'=D1×(n0/n1). In such a way, by obtaining optical path length d1' which is closer to actual measured object, and by moving image surface SSA2 closer to boundary surface SS2 over the entire scanning range, a tomographic image, which is closer to actual tissue, can be displayed.

It is needles to say that the present invention can be applied to any one of TD (Time Domain)–OCT measurement and FD (Fourier Domain)–OCT measurement.

DESCRIPTION OF THE SYMBOLS

BS: beam splitting means
CL1: first collimator
CL2: second collimator
CNL: condenser lens
DT: interference light detecting means
FB: optical fiber
GM: galvano mirror
ID: inputting means
L: low coherent light
L1: measuring light
L2: reference light
MT: monitor
PC: personal computer
RAM: reference mirror
S: measured object
S1 to S3: layer
SAP2: point
SP1: point
SP2: point
SS1: surface
SS2: boundary surface
SSA2: image surface
SLD: light source
WS1, WS2: wave shapes
t1 to t3: thickness

What is claimed is:

1. An optical tomographic image forming method comprising:
    splitting low coherence light emitted from a light source into a measuring light and a reference light;
    positioning a reference mirror at a predetermined length of optical path away from the splitting position;
    irradiating said measuring light onto a measured object via a condenser lens;
    irradiating said reference light onto said reference mirror;
    superposing a reflected light reflected from said measured object and a reflected light reflected from said reference mirror to detect an interference light; and
    forming an optical tomographic image of said measured object by the detecting the interference light,
    wherein the method further comprises:
    inputting a refractive index of said measured object;
    correcting said tomographic image in accordance with the inputted refractive index of said measured object; and
    outputting the corrected tomographic image,
    wherein the method further comprises:
    moving at least one of said measured object, said condenser lens, and said reference mirror along an optical path to obtain a first position of said measured object, said condenser lens, and said reference mirror in which the intensity of an interference light of a reflected light reflected from said first reflecting surface and a reflected light from said reference mirror is maximized;
    moving said measured object or said condenser lens along said optical path, while holding said reference mirror at the first position, to obtain a second position in which the intensity of an interference light of a reflected light reflected from said second reflecting surface and said reflected light from said reference mirror is maximized,
    moving said reference mirror along said optical path, while holding said measured object or said condenser lens at the first position, to obtain a third position in which the intensity of an interference light of a reflected light reflected from the second reflecting surface and said reflected light from said reference mirror is maximized; and
    obtaining said refractive index of said measured object based on the first position, second position and the third position.

2. The optical tomographic image forming method of claim 1, wherein a known datum is being inputted as said refractive index of said measured object.

3. The optical tomographic image forming method of claim 1, wherein, in a case in which said measuring light is incident upon a first reflecting surface of said measured object obliquely to the first reflecting surface, the method further comprises:
    irradiating said measuring light upon a first reflecting surface of said measured object obliquely to the first reflecting surface to refract the measurement light;
    replacing an optical path length of said refracted light from the first surface to the second surface by an optical path length between said first reflecting surface and said second reflecting surface in said straight line of said incident angle;
    correcting said optical tomographic image in accordance with said replaced optical path length and in accordance with a refractive index between said first reflecting surface and said second reflecting surface; and
    outputting the corrected tomographic image.

4. The optical tomographic image forming method of claim 1, wherein, in a case in which said measuring light is incident upon a first reflecting surface of said measured object obliquely to the first reflecting surface, the method further comprises:

irradiating said measuring light upon a first reflecting surface of said measured object obliquely to the first reflecting surface to refract the measurement light;

determining an optical path length of said refracted light from the first surface to the second surface in accordance with: an incident angle of said measuring light upon said first reflecting surface, a refractive index of an incident side of said first reflecting surface, and a refractive index between said first reflecting surface and said second reflecting surface;

correcting said optical tomographic image in accordance with the determined said optical path length between said first reflecting surface and said second reflecting surface; and outputting the corrected tomographic image.

5. The optical tomographic image forming method of claim 1, wherein coherency distance $\Delta l$ of said low coherence light, which is expressed by the following equation, is less than or equal to 30 µm:

$$\Delta l = 2(\ln 2)\lambda_o^2/(\pi \Delta \lambda)$$

where $\lambda_o$: Center wavelength of said low coherence light, and $\Delta \lambda$: Bandwidth of said low coherence light (range of intensity more than or equal to half of the maximum intensity).

6. The optical tomographic image forming method of claim 1, wherein said refractive index of said measured object is obtained based on a distance of the first position and second position and a distance of the first position and the third position.

\* \* \* \* \*